United States Patent [19]
Weinheimer et al.

[11] Patent Number: 6,036,171
[45] Date of Patent: Mar. 14, 2000

[54] SWABBABLE VALVE ASSEMBLY

[75] Inventors: Jacek M. Weinheimer, Treasure Island; Edward Welling, Seminole, both of Fla.

[73] Assignee: Halkey-Roberts Corporation, St. Petersburg, Fla.

[21] Appl. No.: 09/174,792

[22] Filed: Oct. 19, 1998

Related U.S. Application Data

[63] Continuation-in-part of application No. 09/151,378, Sep. 10, 1998
[60] Provisional application No. 60/059,323, Sep. 17, 1997.
[51] Int. Cl.$^7$ .......................... A61M 39/26; F16K 51/00
[52] U.S. Cl. ..................... 251/149.1; 251/149.4; 604/33; 604/905
[58] Field of Search ............ 251/149.1, 149.4, 251/149.6; 222/501; 604/33, 83, 246, 249, 905

[56] References Cited

U.S. PATENT DOCUMENTS

| | | |
|---|---|---|
| 3,806,086 | 4/1974 | Cloyd . |
| 4,917,668 | 4/1990 | Haindl . |
| 5,080,654 | 1/1992 | Picha et al. . |
| 5,108,380 | 4/1992 | Herlitze et al. . |
| 5,242,393 | 9/1993 | Brimhall et al. . |
| 5,330,435 | 7/1994 | Vaillancourt . |
| 5,349,984 | 9/1994 | Weinheimer et al. . |
| 5,360,413 | 11/1994 | Leason et al. . |
| 5,380,306 | 1/1995 | Brinon . |
| 5,474,536 | 12/1995 | Bonaldo . |
| 5,474,544 | 12/1995 | Lynn . |
| 5,509,433 | 4/1996 | Paradis . |
| 5,509,912 | 4/1996 | Vaillancourt et al. . |
| 5,520,666 | 5/1996 | Choudhury et al. . |
| 5,533,708 | 7/1996 | Atkinson et al. . |
| 5,549,566 | 8/1996 | Elias et al. . |
| 5,616,130 | 4/1997 | Mayer . |
| 5,699,821 | 12/1997 | Paradis ................................ 251/149 |
| 5,820,601 | 10/1998 | Mayer ................................ 251/149.1 |

OTHER PUBLICATIONS

SoloPak Maxcess Needleless System, SoloPak Pharmaceuticals, Inc., two page brochure.
The MMG MLI–Set, MMG Infusion Technologies, one page brochure.
Clave Connector, Clave1, Rev. Mar. 1994, two page brochure.
Smart Site Needleless System, Alaris Medical Systems Inc., two page brochure, May 1997.
Safe Connect, Winfield Medical, 10 page brochure.
Quality Check Valves from Burron, Burron Medical Inc., one page brochure.

*Primary Examiner*—Kevin Shaver
*Assistant Examiner*—Eric Keasel
*Attorney, Agent, or Firm*—Trexler, Bushnell, Giangiorgi & Blackstone, Ltd.

[57] ABSTRACT

Disclosed is a female-type valve engageable with a male component or instrument, where the valve includes a deformable stem which is located in a valve body and is shiftable therein to receive said instrument in sealed engagement. When an instrument is engaged with an aperture in the stem, the stem shifts in the valve body and the aperture deforms to seal against said instrument and allow liquid to flow through the stem, to or from the instrument. A plug member is carried by the stem, and the plug member can shift to a position of generally sealed engagement with the stem, or it can be displaced by the instrument to permit fluid flow. The plug can reseat upon initial retroactive movement of the instrument, while the instrument is still engaged with the aperture in the stem.

20 Claims, 4 Drawing Sheets

SWABBABLE VALVE ASSEMBLY

CROSS-REFERENCE

This application is a Continuation-In-Part application of U.S. patent application Ser. No. 09/151,378, filed Sep. 10, 1998 which claims the benefit of U.S. Provisional Application No. 60/059,323, filed Sep. 17, 1997.

BACKGROUND

The present invention relates generally to valves, and relates more specifically to a novel valve construction that provides many improved features over the prior art, and is well adapted for medical usage, such as in needleless IV sets, and other medical applications where it is desirable to avoid use of needles in the transmission and delivery of fluid products to patients in a sterile environment.

Presently, there are many types of valves, such as check valves, which are designed to control the one-way flow of a fluid therethrough. One common type of check valve comprises a valve element, such as a ball or a spring biased valve stem, reciprocatingly positioned within a valve body providing a fluid passageway. The flow of fluid in one direction through the valve body is permitted upon displacement of the stem as it flows around the valve element to exit the valve body. However, in the opposite direction, the flow of fluid along with the spring forces the valve element against a valve seat, thereby inhibiting, or checking, the flow of fluid therethrough. In this manner, this type of check valve effectively provides that fluid can flow only in one direction through the check valve. An example of this type of valve can be found in U.S. Pat. No. 5,349,984.

Instead of necessitating fluid flow in an opposite direction in order to provide that the valve element is forced into the valve seat, some check valves provide means associated with the valve element for constantly urging the valve element into the valve seat. For example, a compression spring is often disposed within the valve body for this purpose. Because of the constant urging of the valve element into the valve seat by the compression spring, some amount of pressure must be exerted on the valve element to unseat same from the valve seat and allow fluid to flow therepast.

The check valves described above provide several disadvantages. For example, while the seating of the valve element in the valve seat provides that fluid cannot flow therepast, this does not provide that the end of the check valve body is sealed. As a result, bacteria or other contaminants may enter the valve body and accumulate in the valve body between the end of the valve body and the seated valve element. Additionally, often the valve element is disposed in the valve body some distance from the end of the valve body, therefore it may prove difficult to adequately clean or sterilize the check valve. In many applications, it is important to provide that the check valve is kept clean and sterile, such as in medical applications when, for example, fluid is being injected therethrough into a patient.

Moreover, in the case where a check valve is provided with a compression spring for urging the valve element into the valve seat, the fluid traveling through the check valve contacts the compression spring. In fact, fluid or other material on the other side of the check valve can contact the compression spring even when the valve element is seated in the valve seat. As a result, certain material can build up on the compression spring. For example, corrosion can build up on the compression spring over time, some metallic components can leach into the fluid, or, within a medical application, bacteria can build up on the compression spring.

Because incoming fluid contacts the compression spring as the fluid flows through the check valve, the material which has built up on the compression spring may join the incoming fluid and flow out the check valve along with the incoming fluid. This is undesirable in most situations, and is especially undesirable within medical applications where sterility is a priority. Check valves in the medical field often provide even more areas at which bacteria can collect.

Furthermore, in medical applications, it is usually desirable to prevent the patient from being exposed to the fluid which is being injected to or extracted from the patient, and insulate nurses and doctors from exposure to the liquid which may contain the patient's blood or waste products. However, often the instrument used to inject or withdraw the fluid which is generally the male component of the valve set, retains some of the fluid on the tip thereof, thus providing a risk to nurses and doctors of being exposed to the fluid. Additionally, thermal valve components into which the male component or instrument is inserted have a tendency, due to residual pressure, for fluid near the end of the female valve component to spray out of the valve into the air upon withdrawal of the male component or instrument from the valve thereby exposing nurses, doctors and attendants, other than the patient, to the fluid being injected or extracted.

The present invention is directed to address the problems encountered heretofore which are discussed hereinabove.

OBJECTS AND SUMMARY OF THE DISCLOSURE

A general object of the present invention is to provide a valve which seals itself to restrict fluid flow thereinto, and decreases the risk of contaminants such as bacteria collecting on or within the valve. All external surfaces in the proximity of the valve stem are accessible to be wiped clean with a sterile swab.

Another object of the present invention is to provide a valve which restricts fluid flow therethrough without requiring fluid pressure in the opposite direction and which does so without providing a compression spring that is exposed to fluid or liquid being handled by the valve.

Still another object of the present invention is to provide a valve structure including a female valve component which seals with a male component or instrument when the instrument is engaged therewith so that there is no leakage of fluid.

Yet another object of the present invention is to provide a valve which automatically wipes or swabs the male component or instrument upon the instrument being disengaged or removed therefrom.

A still yet further object of the present invention is to provide a valve structure, and particularly a female valve which obtains an effective seal and does not have a tendency to spray fluid into the surrounding area upon the male component or instrument being disengaged therefrom.

Yet still another object of the present invention is to provide a valve structure which allows fluid flow in both directions upon a male component or instrument being engaged therewith.

Briefly, and in accordance with the above, the present invention envisions a valve or female component engageable with a male component or instrument, where the valve includes a resilient, deformable stem which is located in a valve body and is shiftable therein. When an instrument is engaged in an aperture in the stem, the stem shifts in the valve body and the aperture deforms to conform to and seal against the outer surface of the instrument or male member, thus allowing liquid to flow through the stem, to or from the instrument. A plug member is disposed within the stem. The plug member is normally in sealed engagement with the stem when the valve member is pressurized. Upon insertion of the instrument or male component into the stem, the plug is engaged by the tip of said instrument and moved axially to a seated, non-sealing position. The structure of the valve body and plug are such that when the plug is in this position, fluid can flow in either direction through the valve. As the instrument is removed from the stem, the plug is moved axially by residual pressure to attain sealed engagement with the stem before the instrument is removed entirely from said stem. This prevents spraying of fluid produced upon further removal of the instrument. Also, the stem configuration will swab or clean the tip of the instrument upon removal.

BRIEF DESCRIPTION OF THE DRAWINGS

The organization and manner of the structure and function of the invention, together with further objects and advantages thereof, may be understood by reference to the following description taken in connection with the accompanying drawings, wherein like reference numerals identify like elements, and in which.

DESCRIPTION

Figure 1:
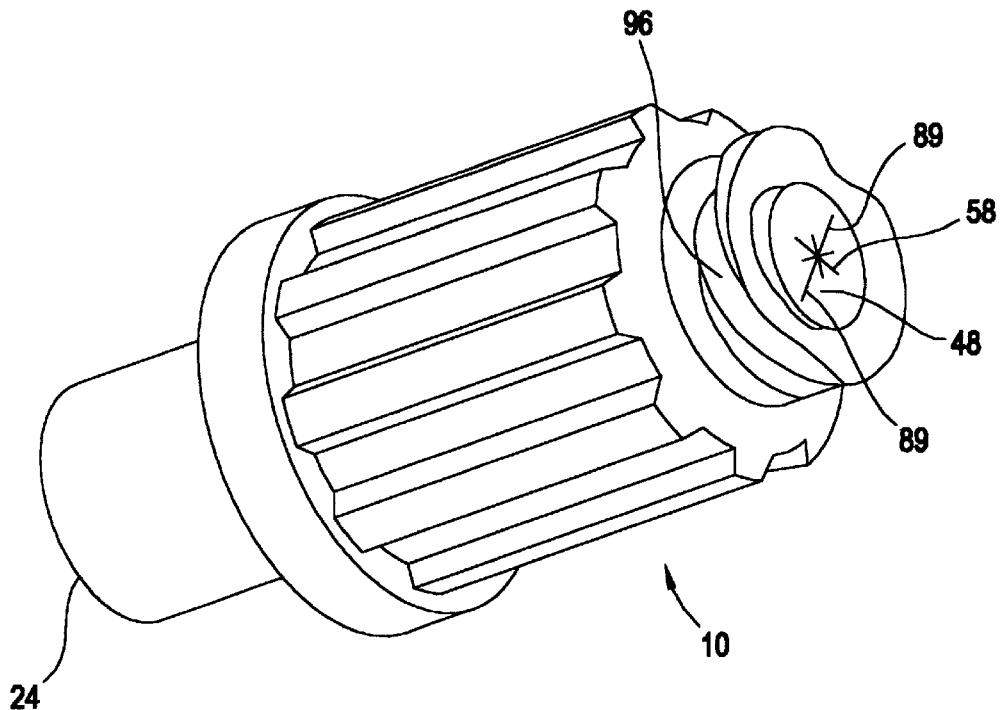
FIG. 1 is an enlarged isometric view of a valve in accordance with the present invention.

Shown in the drawings is a valve, and portions thereof, which is in accordance with an embodiment of the present invention. The valve permits flow in either direction and seals to restrict fluid flow therethrough when the male component or instrument is disengaged. Also, the valve provides a seal with a tip of an instrument when the tip is engaged therewith and automatically wipes or swabs the tip of the instrument clean upon the instrument being disengaged therefrom. All external surfaces in the proximity of a stem in the valve are accessible to be wiped clean with a sterile swab. Further, the valve allows fluid flow in both directions, and does not expose an interior neutral area of the valve to the fluid flowing through the valve, since engagement of the instrument tip with the stem, deforms and compresses the stem into sealed contact with the valve housing. Finally, the valve reduces the likelihood that fluid will spray out from the valve into the surrounding environs when the instrument is disengaged therefrom. Therefore, the valve is specifically directed towards alleviating many problems encountered in the prior art, and provides a sterile fluid path for the delivery or withdraw of fluid to or from a patient.

The valve 10 is shown in FIGS. 1–6, and the remaining Figures, FIGS. 7–15, depict certain individual components of the valve 10 which are shown isolated from the valve for clarity. The valve 10 shown in FIGS. 1–6 includes a substantially tubular valve body 12 having, as shown in FIGS. 3–6, a central axial bore 14 forming an enlarged diameter section 16 and a reduced diameter section 18. The bore 14 defines a first open end 20 for receiving a male valve component or instrument 22, such as a needleless syringe having a cannula tip, and a second open end 24 for communication with a fluid line (not shown). Preferably, the valve body 12 is comprised of a relatively rigid, durable material such as a thermoplastic material.

As shown most clearly in FIGS. 3–6, for ease of assembly, the valve body 12 may be formed of two portions, a female front body portion 26 and a male back end portion 28, which are ultrasonically sealed together at a weld joint 30 to provide the continuous valve body 12. Ultimately, it should be appreciated that the location of the joint 30 is not imperative, and that the valve body 12 need not even be formed of two separate pieces that are connected together, but may be formed of even more pieces or may be formed as a unitary, single-bodied piece. As an alternative to the weld joint 30, a snap joint or a glued joint may be provided between the female front portion 26 and the male rear portion 28 of the valve body 12.

Within the valve body 12 is a stem 32. Preferably the stem 32 is comprised of silicone, but the stem 32 may instead be formed of some other resilient elastomer material, such as natural rubber, a thermoplastic elastomer, or a thermoplastic rubber. As shown in FIGS. 7–10, the stem 32 preferably has a generally conical front body portion 34 and a generally cylindrical rear body or throat portion 36. The front portion 34 includes opposing conical surfaces 42 which are adjacent opposing arcuate flat surfaces 44. As shown, each of the arcuate surfaces 44 begins at a corresponding flat 46 at an end surface 48 of the stem 32, and, while certainly not imperative to the present invention, terminates at the enlarged generally cylindrical rear body portion 36. Additionally, each of the conical surfaces 42 begins at a corresponding generally cylindrical end portion 50 and terminates at the generally cylindrical rear body portion 36. The intersection 52 between each conical surface 42 and corresponding cylindrical end portion 50 is preferably arcuate, and the cylindrical end portions 50 terminate at the end surface 48 of the stem 32.

The rear body portion 36 of the stem 32 is preferably substantially cylindrical to provide strong axial compression resistance, and terminates at a blunt or flat end 54 of the stem 32 opposite the end surface 48. The generally cylindrical end portions 50 assist in closing the aperture 58 in the state depicted in FIGS. 3 and 4, but the same may be accomplished without including the cylindrical end portions 50, but solely by the conical surfaces 42 and flats 44 terminating at the end surfaces 48.

Figure 3:
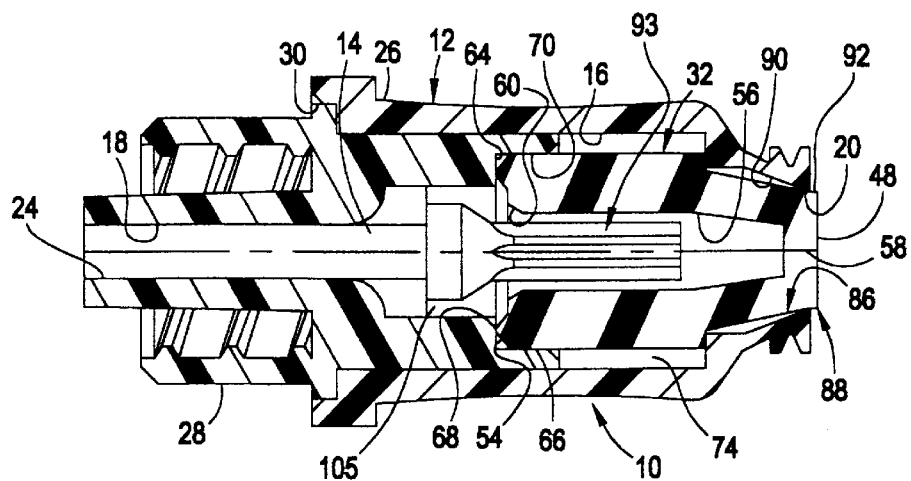
FIG. 3 is an enlarged, cross-sectional view, taken along line 3—3 of FIG. 2, of the valve shown in FIGS. 1 and 2, showing the valve in a non-pressurized state.
Figure 4:
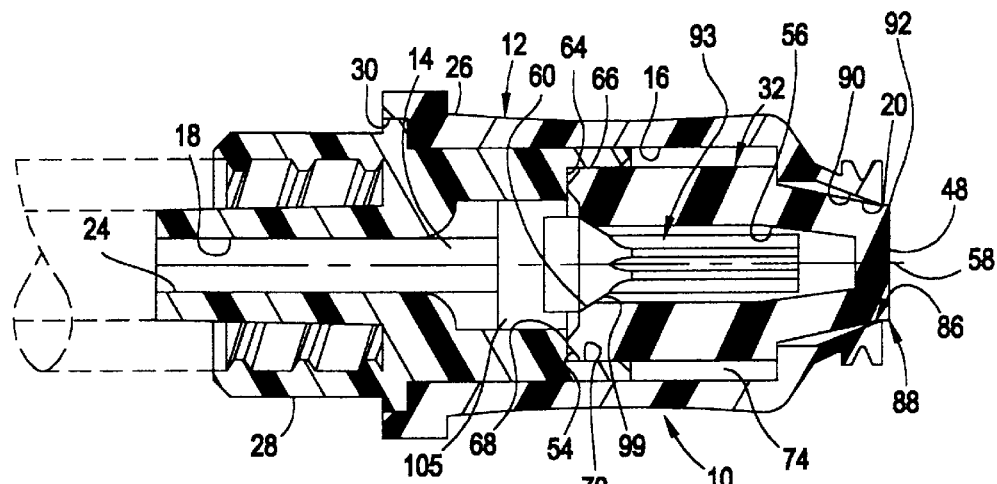
FIG. 4 is an enlarged, cross-sectional view, much like FIG. 3, of the valve of FIGS. 1 and 2, showing the valve in a pressurized state.

As shown in FIGS. 3–6, the stem 32 has a central axial fluid passageway 56 therethrough which defines, at one end of the passageway 56, an aperture 58 in the end surface 48 of the stem 32 and, at the other end of the passageway, defines an opposite, second end opening 60. While the second end opening 60 of the stem 32 is always open, the aperture 58 in the head portion 34 of the stem 32 is in the assembled condition compressed or constricted to a closed position initially forming an internal hermetic seal as shown in FIGS. 1, 3 and 4. However, as shown in the progression from FIG. 4 to FIG. 5 to FIG. 6, the aperture 58 can be deformed to an opened condition by engaging a tip 62 of an instrument 22 therewith, such as the tip of a needleless syringe as will be described more fully later herein.

As shown in the assembled condition of FIGS. 3–6, the end 54 of the body portion 36 defines the second end opening 60 of the stem 32, and this end 54 is seated against a shoulder 64 within the valve body 12, thereby forming a sealed contact therebetween. To provide for an exceptional sealed contact, the end 54 of the body portion 36 is provided with both a flat portion 66 adjacent the end 54 and a lip 68 which protrudes from the end 54. While the lip 68 seals against the shoulder 64 within the valve body 12, the flat portion 66 seals against an adjacent internal side wall 70 within the valve body 12 thereby providing essentially two contact surfaces between the end 54 of the stem 32 and the valve body 12. One having ordinary skill in the art may recognize other ways in which to provide an exceptional sealed contact between the stem 32 and the valve body 12. As shown, preferably the second end of the stem 32 aligns with an internal surface of the valve body 12 thus providing a smooth fluid flow path between the fluid passageway 56 in the stem 32 and the valve body 12 for carrying a liquid, air or other fluid within the valve 10. Providing sealed contact between the end 54 of the stem 32 and the valve body 12 is important in order to prevent fluid from entering or leaking into the neutral space 74 between the stem 32 and the valve body 12 from the fluid flow area 72. Leaking of fluid into the neutral space 74 can result in the leaking of fluid therefrom out the end 20 of the valve body 12 as well as provide other disadvantages which will be discussed more fully later herein.

Figure 5:
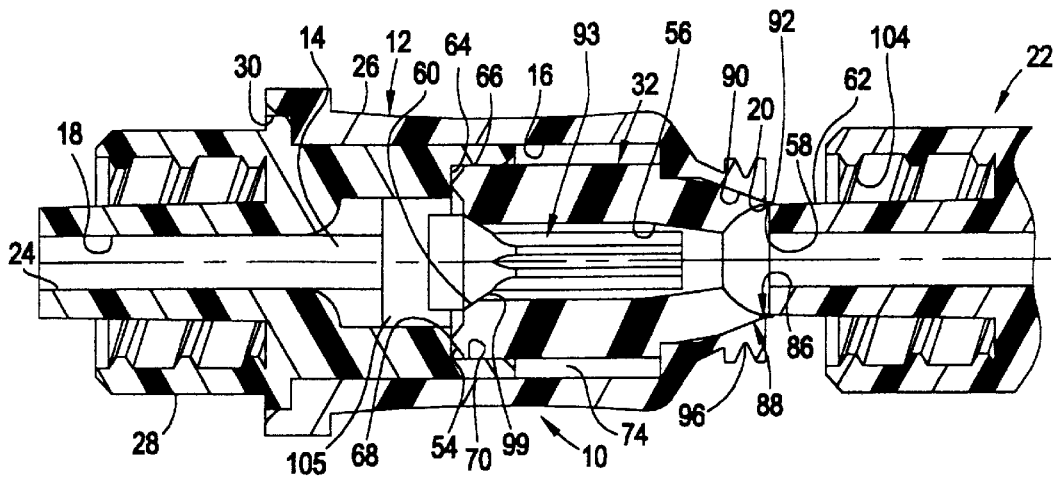
FIG. 5 is an enlarged, cross-sectional view, much like FIG. 4, of the valve of FIGS. 1 and 2, showing a tip of an instrument being engaged with an aperture in a stem of the valve.
Figure 6:
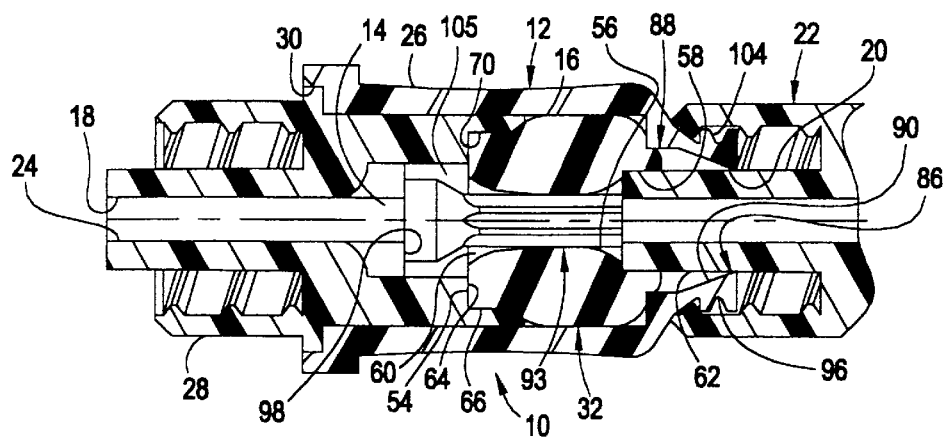
FIG. 6 is an enlarged, cross-sectional view, much like FIG. 5, of the valve of FIGS. 1 and 2, showing the tip of the instrument fully received by the aperture in the stem, and showing fluid being injected from the instrument into the valve.

The stem 32 is preferably configured such that it is naturally urged in the valve body 12 into the position shown in FIGS. 1, 3 and 4. However, means may be provided for urging the end 48 of the stem 32 towards the end 20 of the valve body 12. Particularly, a compression spring (not shown) may be provided in the neutral space 74 between the stem 32 and the valve body 12. To this end, the stem 32 may be provided with an outwardly extending shoulder on the front body portion 34 for engaging an end of the compression spring, and the valve body 12 may be provided with a shoulder for engaging the other end of the compression spring. In this manner, the compression spring can compress between the stem 32 and the valve body 12 and urge the end 48 of the stem 32 towards the end 20 of the valve body 12. Compression would result from the tip 62 of the instrument 22 being inserted into the aperture 58 at the end 48 of the stem 32, which insertion will be described more fully later herein. FIGS. 1–4 show the valve 10 when the tip 62 of the instrument 22 is not so engaged and FIGS. 5 and 6 show the valve 10 when the tip 62 of the instrument 22 is engaged therewith. At either time, the compression spring would tend to restore itself to its free length, but would only be able to reach a pre-loaded state.

Should a compression spring be provided between the stem 32 and the valve body 12, it becomes even more important to prevent fluid from leaking into the neutral space 74 between the stem 32 and the valve body 12 from the fluid flow area. Leaking of fluid into the neutral space 74 can cause a compression spring to corrode or leach metallic components over time, and subsequently the corrosion or leached metals can escape back into the fluid flow area mixing with the flowing fluid. Or, within a medical application, leaking of fluid into the neutral space 74 can cause bacteria to collect on the compression spring, and subsequently the bacteria can escape back into the fluid flow area mixing with the flowing fluid and exposing a patient thereto.

Instead of providing a compression spring between the stem 32 and the valve body 12, the stem 32 is configured such that in the assembled condition, it is compressed and due to its inherent resiliency is urged into position, and this is what is depicted and preferred. For example, the rear body portion 36 of the stem 32 may be provided as having a thick wall and being robust enough to provide a sufficient spring rate or force in order to urge the end 48 of the stem 32 towards the first end 20 of the valve body 12. In this event, the stem 32 would be assembled in a compressed condition with the inherent resiliency of the material from which the stem 32 is constructed providing the necessary spring force to urge the stem to the position as shown in FIGS. 1, 3 and 4 wherein the aperture 58 is biased to a closed, sealed condition, as discussed hereinafter. As such, the rear body portion 36 may include longitudinal ribs (not shown) or the like to strengthen this section, yet provide resiliency, as shown in U.S. Pat. No. 5,349,984, which is incorporated herein by reference. Of course, even should a compression spring not be included, it remains desirable to prevent the leaking of fluid into the neutral space 74 and the present invention provides as such. One having ordinary skill in the art would likely recognize still other types of means which may be provided for urging the end 48 of the stem 32 towards the end 20 of the valve body 12 while remaining totally within the scope of the present invention.

As shown in FIGS. 3–6, the forward end of the valve body 12 has stem-engaging structure 86 near the first end 20 thereof for engaging with the front body portion 34 of the stem 32 when the end 48 of the stem 32 is urged towards the first end 20 of the valve body 12 when the tip 62 of the instrument 22 is not engaged therewith, as shown in FIGS. 3 and 4. Likewise, the stem 32 has valve body-engaging structure 88 (see also FIGS. 7–10) near the end 48 thereof for engaging with the valve body 12 when the end 48 of the stem 32 is urged towards the first end 20 of the valve body 12. This engagement between the stem 32 and the valve body 12 provides that the aperture 58 on the end 48 of the front body portion 34 of the stem 32 is urged closed when the end 48 of the stem 32 is urged towards the first end 20 of the valve body 12 and the tip 62 of an instrument 22 is not engaged therewith.

As shown, the stem-engaging structure 86 on the valve body 12 may comprise a taper 90 near the end 20 thereof. Preferably, the taper angle of the taper 90 is more than the generally conical front body portion 34 of the stem 32 of the stem 32. The valve body-engaging structure 88 on the stem 32 may comprise contact points 92 for engaging with the taper 90 at the end 20 of the valve body 12. When the end 48 of the stem 32 is urged towards the first end 20 of the valve body 12, as shown in FIGS. 3 and 4, the taper 90 of the valve body 12 presses axially and radially against the contact points 92 on the head portion 34 of the stem 32 thereby urging the contact points 92 of the stem 32 towards each other. This urging causes the aperture 58 on the end 48 of the stem 32 to radially compress (as represented by arrows 89 in FIG. 1), and therefore close, with enough force to contain any internal pressure located in the axial passageway 56 of the stem 32. When the aperture 58 is fully closed, the contact points 92 of the stem 32 project axially slightly past the extreme end of the end 20 of the valve body 12. This projection of the end 48 of the head portion 34 past the extreme end of the end 20 of the valve body 12 can be seen in FIGS. 1, 3 and 4, and provides that the end 48 of the stem 32 and adjacent areas can be cleaned. This feature is important in medical applications where bacteria growth is to be avoided. To this end, a sterilizing swab can be used to clean the end 48 of the stem 32 and adjacent protruding areas.

Figures 7, 8:
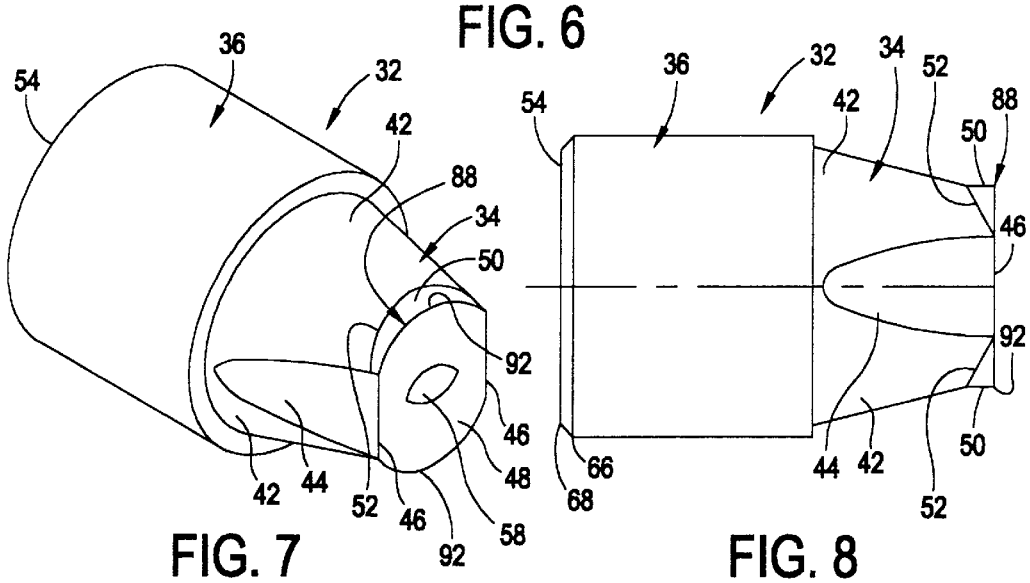
FIG. 7 is an enlarged isometric view of a stem component of the valve illustrated in the previous Figures.
FIG. 8 is a side, elevational view of the stem depicted in FIG. 7.
Figures 9, 10:
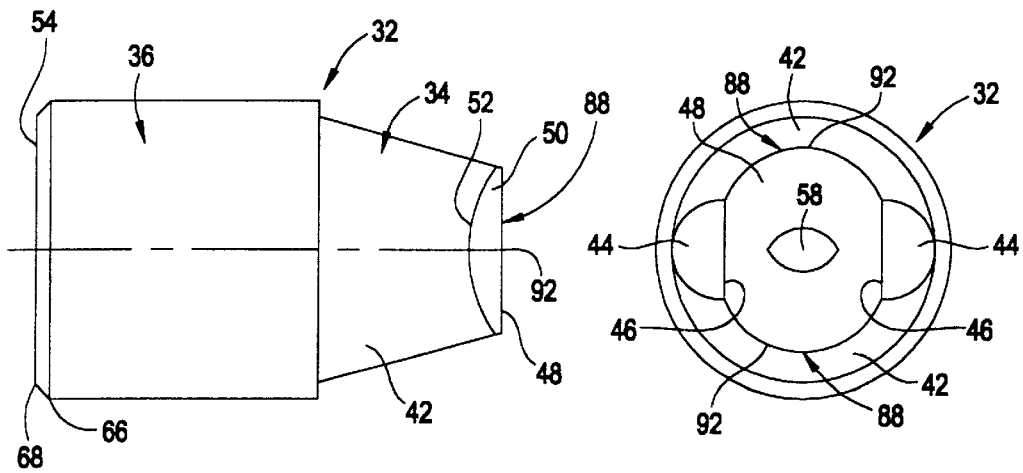
FIG. 9 is a top, plan view of the stem depicted in FIG. 7.
FIG. 10 is a front, elevational view of the stem depicted in FIG. 7.

To further facilitate the closing of the aperture 58 when the tip 62 of an instrument 22 is not engaged therewith, the aperture 58 can be oval or oblong shaped as shown in FIGS. 7 and 10. The aperture 58 shown is formed by the intersection of two offset circles. Specifically, preferably the aperture 58 has a minor axis aligned with the contact points 92 on the stem 32, and has a major axis aligned with the flats 46 of the stem 32, perpendicular to the contact points 92. As shown, the contact points 92 are adjacent the flats 46 on the stem 32. The diametral distance of the contact points 92 is greater than the diametral distance of the adjacent flats 46 (e.g., the diametral distance of the flats 46 is defined as the diameter of a circle just touching the flats 46 at the end 48). This enables the contact points 92 to receive most of the radial compression from the taper 90, closing the aperture 58 at its minor axis, or narrowest opening, in the direction indicated by arrows 89 in FIG. 1.

As shown in FIGS. 3–6, a plug member 93 is located within the valve 10 and at least partially within the stem 32. Preferably, the plug member 93 is free-floating in that the valve 10 is not attached to any of the other components thereof. The plug member 93 is preferably generally coaxially centered with respect to the remainder of the valve 10, and is substantially contained in and is movable or shiftable within the stem 32.

Figure 11:
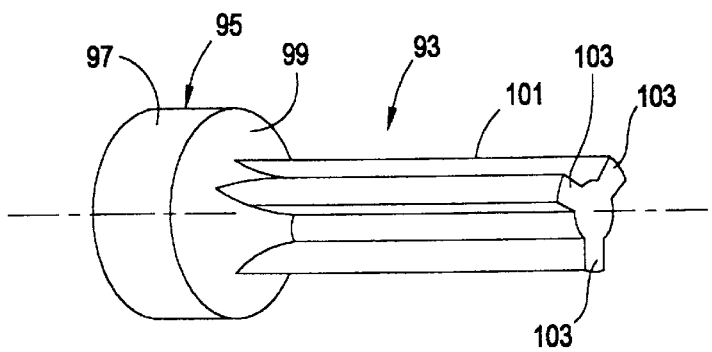
FIG. 11 is an isometric view of a plug member component of the valve illustrated in FIGS. 1–6.
Figure 12:
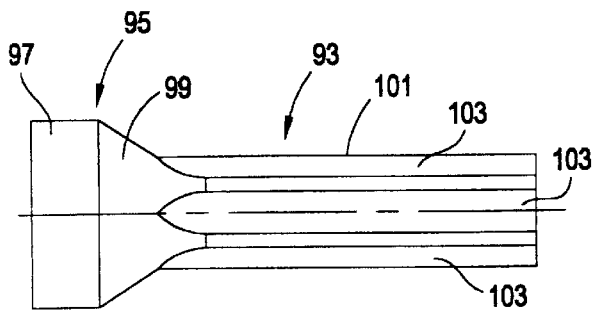
FIG. 12 is a top, plan view of the plug member depicted in FIG. 11.
Figure 13:
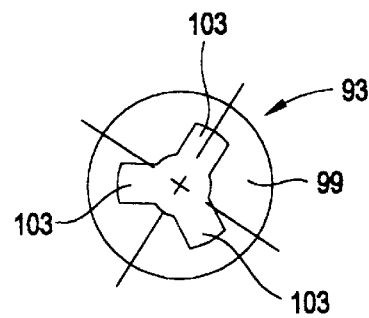
FIG. 13 is a front, elevational view of the plug member depicted in FIG. 11.

In FIGS. 11–13, the plug member 93 is shown isolated from the remainder of the valve 10 for clarity. As shown, the plug member 93 includes an end portion 95 which includes a generally cylindrically-shaped segment 97 and an adjacent, generally conical portion 99. Extending from the generally conical portion 99 is an elongated or longitudinal portion 101. The longitudinal portion 101 includes a plurality of fins 103 which extend along the length of the longitudinal portion 101 and terminate at the generally conical portion 99. As will be described, when the valve is in an operable situation, viz., connected to instrument with fluid flow, fluid can flow between the fins 103 of the plug member 93 within the axial passageway 56 of the stem 32.

FIG. 3 depicts the situation where the valve is not connected to a male component or instrument, and there is no fluid pressure being exerted on the valve 10. Such a condition may be present in the case where the valve 10 is not connected to a fluid line. At this time, the plug member 93 is free to float within the valve 10 as the plug member is not attached to or securably engaged with any of the other components of the valve 10. Specifically, the end portion 95 of the plug member 93 can float within area 105.

In contrast to FIG. 3, FIG. 4 depicts the situation where there is fluid pressure being exerted on the end portion 95 of the plug member 93. Such a condition would be present if the valve body 12 were to be connected to a fluid line, shown in phantom in FIG. 4. In this case, the fluid pressure from the fluid line acts on the end surface of the plug 93 and forces or urges the plug member 93 axially into sealed contact with the end 54 of the stem 32. Specifically, the conical portion 99 of the plug member 93 abuts the end 54 of the stem 32 and forms a seal therewith. This seal provides that fluid cannot travel between area 105 and the central axial fluid passageway 56 of the stem 32 unless the plug member 93 is unseated from against the end 54 of the stem 32.

Directing attention now to FIG. 5, when a tip 62 of an instrument 22 is initially engaged with the aperture 58 in the end 48 of the stem 32, the plug member 93 remains sealed with the end 54 of the stem 32. This provides that the central axial fluid passageway 56 of the stem 32 and area 105 remain at their separate, respective pressures. The plug member 93 remains sealed with the end 54 of the stem 32 because the longitudinal portion 101 of the plug member 93 does not reach the end 54 of the stem 32 when the plug member 93 is in the sealed position. Therefore, to unseat the plug member 93, the tip 62 of the instrument 22 need not only be engaged with the aperture 58 in the end 54 of the stem 32, but the tip 62 of the instrument must be moved sufficiently axially into the stem 32 until the tip 62 of the instrument 22 contacts and displaces the plug member 93, FIG. 6. As a result of requiring that the tip 62 of the instrument must be moved sufficiently axially into the stem 32 until the tip 62 of the instrument 22 contacts the plug member 93 before the plug member 93 unseats from against the end 54 of the stem 32, a seal is achieved between the tip 62 of the instrument 22 and the aperture 58 in the end 48 of the stem 32 before the seal between the plug member 93 and the stem 32 is broken. Hence, fluid cannot spray from area 105 out of the aperture 58 of the stem 32 as the tip 62 of the instrument 22 is initially engaged therewith. Additionally, fluid cannot spray out the aperture 58 when the plug member 93 is eventually unseated from the end 54 of the stem 32 because of the seal formed between the tip 62 of the instrument 22 and the aperture 58.

Figure 14:
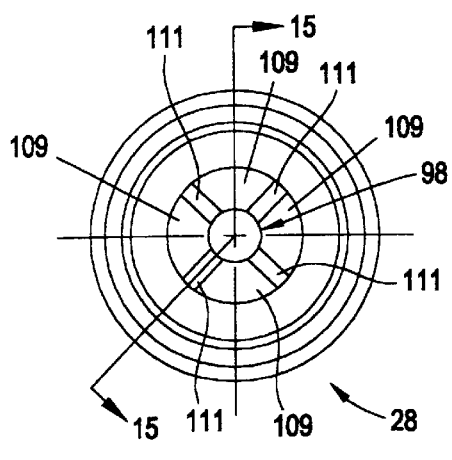
FIG. 14 is a top, plan view of a portion of a body of the valve which is shown in FIGS. 1–6.
Figure 15:
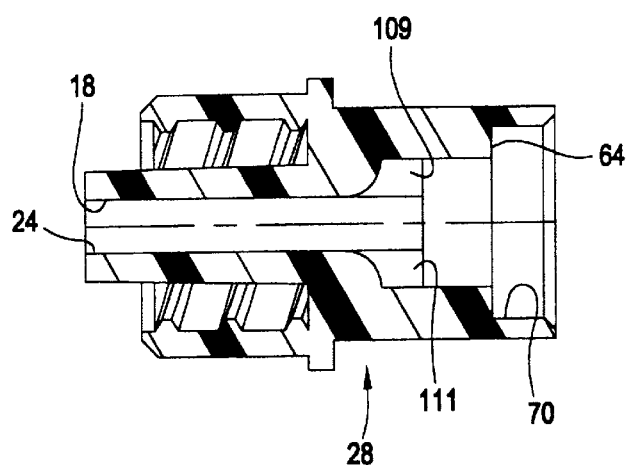
FIG. 15 is a side, cross-sectional view of the body portion shown in FIG. 14, taken along line 15—15 of FIG. 14.

As mentioned, in order to unseat the plug member 93, the tip 62 of the instrument must be moved sufficiently axially along the valve 10 in the stem 32 until the tip 62 of the instrument 22 contacts and displaces the plug member 93. This is shown in FIG. 6. As shown, the pressing of the tip 62 of the instrument 22 on the plug member 93 causes the conical portion 99 of the plug member 93 to unseat from the end 54 of the stem 32. The plug 93 will engage an apertured seat 98, the structure of which is shown in FIG. 14. As a result, fluid flow is possible in either direction within the valve 10, between area 105 and the central axial fluid passageway 56 of the stem 32. As discussed above, fluid can flow between the fins 103 of the longitudinal portion 101 of the plug member 93, and past the apertured seat 98. Additionally, as shown in FIG. 14, the component portion 28 of the valve body 12 provides the apertured plug seat 98, which includes fluid passageways 109 which are separated by webs or fins 111 (see also FIG. 15). Hence, fluid can flow from between the fins 103 of the plug member 93 and past seat 98 and into the fluid passageways 109 (and vice versa depending on the direction of the fluid flow).

Figure 2:
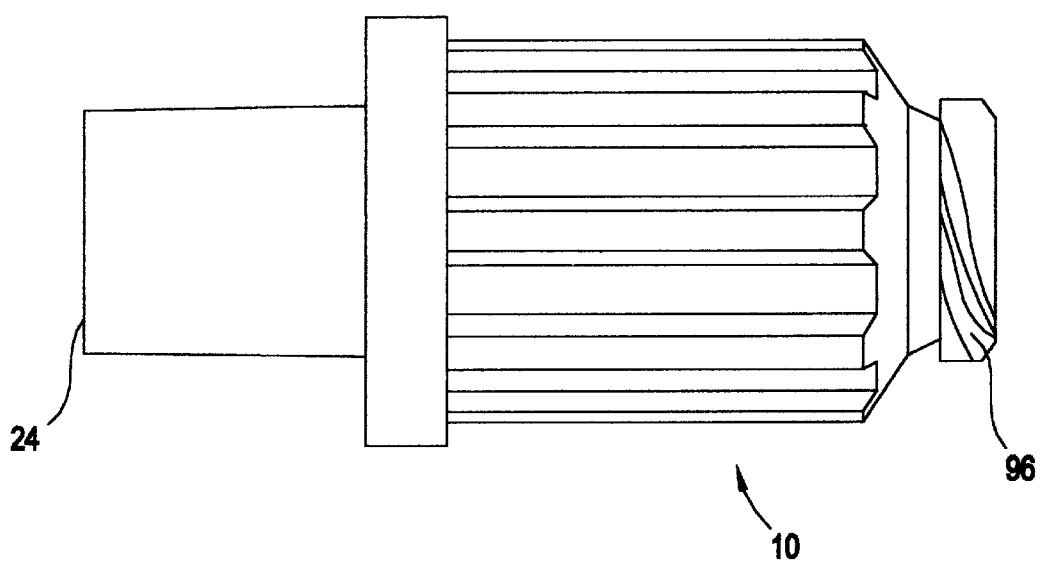
FIG. 2 is an enlarged, side elevational view of the valve shown in FIG. 1.

Operation of the valve 10 shown in FIGS. 1–6 will now be described in connection with engagement of an instrument 22 therewith. As mentioned, the instrument 22 to be engaged with the valve 10 may be a needleless syringe having a cannula tip. Before the instrument 22 is engaged with the valve 10, the valve 10 is in the condition as shown in FIGS. 1, 2, and either FIG. 3 or 4 depending on whether the valve 10 is connected to a fluid line. At that time, the end 48 of the stem 32 is sealed with the valve body 12, and the stem 32 is urged into the position shown in FIGS. 1, 3 and 4 where the end 48 of the stem 32 protrudes slightly out from the end 20 of the valve body 12. This urging of the stem 32 into this position causes the taper 90 on the valve body 12 to press axially and radially against the contact points 92 on the front body portion 34 of the stem 32, thus causing the aperture 58 on the end 48 of the front body portion 34 of the stem 32 to radially compress. This compression is with enough force to cause the aperture 58 to close and seal as shown in FIGS. 1, 3 and 4, thus containing any internal pressure within the stem 32. At this time, the aperture 58 in the end 48 of the stem 32 is hermetically sealed. At the opposite end 54 of the stem 32, a seal is created by constant compression of the stem 32 at the two sealing surfaces between the valve body 12 and the flat portion 66 and lip 68 at the end 54 of the stem 32. Additionally, if fluid pressure is present behind the plug member 93 because the valve 10 is connected to a fluid line, the plug member 93 will seat against the end 54 of the stem 32 creating a seal. As mentioned, this is the condition shown in FIG. 4.

When the tip 62 of the instrument 22 is first brought into engagement with the aperture 58 in the end 48 of the stem 32, the aperture 58 initially resists the insertion thereof. However, as the tip 62 of the instrument 22 is further pushed or engaged into the aperture 58, the aperture 58 eventually deforms or opens to allow entry of the tip 62 of the instrument 22, as shown in FIG. 5, and due to the resiliency of stem 32 a tight hermetic seal is formed between the stem 32 and the tip 62 of the instrument 22. The engagement of the tip 62 with stem 32 further serves to compress said stem and enhance the internal seals. During the initial insertion of the tip 62 of the instrument 22 into the aperture 58 in the stem 32, the plug member 93 remains seated (assuming fluid pressure behind the plug member 93) against the end 54 of the stem 32, thereby maintaining the seal. Therefore, fluid cannot flow between area 105 and the central axial fluid passageway 56 of the stem 32. Hence, the seal between the plug member 93 and the stem 32 provides that fluid cannot spray from area 105 out the aperture 58 in the end 48 of the stem 32 before the seal with the tip 62 of the instrument 22 is formed.

As the tip 62 of the instrument 22 is further pushed into the aperture 58 in the stem 32, the tip 62 contacts the plug member 93 causing the plug member 93 to move axially and unseat from the stem 32 as shown in FIG. 6. At this time, fluid can flow in either direction between area 105 and the central axial fluid passageway 56 of the stem 32. Specifically, fluid can flow from the tip 62 of the instrument 22, into the central axial fluid passageway 56 of the stem 32, between the fins 103 on the longitudinal portion 101 of the plug member 93, into the fluid passageways 109 formed in seat 98 of the valve body 12, and out the end 24 of the valve 10. Alternatively, in the other direction, fluid can flow into the end 24 of the valve 10, through the fluid passageways 109 of the valve body 12, between the fins 103 on the longitudinal portion 101 of the plug member 93, and into the tip 62 of the instrument 22.

As shown in FIGS. 5 and 6, a female thread or Luer lock thread 96 (see also FIGS. 1 and 2) may be provided on the valve body 12 near the end 20 thereof for engagement with a corresponding male Luer lock thread 104 on the instrument 22. Or, other corresponding structure may be provided between the valve 10 and the instrument 22 for engagement therebetween. It is preferable to provide the described Luer lock threads or some other engagement structure because the engagement between the valve 10 and the instrument 22 helps to align the instrument 22 while providing a mechanical advantage to overcome the resistance by the aperture 58 to expanding and accommodating the tip 62 of the instrument 22. However, it should be pointed out that engagement between the valve body 12 and the instrument 22 is not necessary to keep the tip 62 of the instrument 22 and the aperture 58 of the stem 32 engaged because the grip or the frictional engagement of the aperture 58 around the tip 62 is sufficient to hold the instrument 22 and the valve 10 in engagement in most cases. Nevertheless, it may be desirable to provide the above-described Luer lock threads 98 and 96 on the instrument 22 and valve body 12, respectively, or some other engagement structure, when large separation forces will be present therebetween. This, of course, will depend on the application in which the valve 10 is used.

After the tip 62 of the instrument 22 is engaged with the aperture 58, fluid may be injected or withdrawn via the tip 62 through the stem 32, that is to say, the instrument 22 may suction or inject fluid through the stem 32. Regardless, fluid can travel axially along the fluid passageway 56 in the stem 32 and the reduced diameter section 18 of the valve body 12. As the fluid flows, no fluid enters the neutral space 74 between the stem 32 and the valve body 12. Therefore, bacteria growth in the neutral space 74 is not encouraged. Additionally, a compression spring, if it were to be provided between the stem 32 and valve body 12, would not be exposed to the fluid passing through the valve 10. Therefore, there can be no leaching of harmful metals into the fluid stream.

Consideration is now directed to what occurs upon disengagement of the instrument 22 from the valve 10. As the tip 62 of the instrument 22 is initially withdrawn from the aperture 58 in the end 48 of the stem 32 (shown in the progression from FIG. 6 to FIG. 5), the stem 32, due to its inherent resiliency, is urged toward the end 48 of the valve body 12 and against the taper 90. As a result of this constant bias of the stem 32 toward the tip 62, the aperture 58 in the stem 32 and adjacent internal stem walls wipe or swab the tip 62 virtually free of fluid as the tip 62 is being withdrawn. In medical applications, this can reduce the waste of expensive injectable solutions and minimize unintended, undesired human exposure to the fluid, which may be contaminated or a biohazardous fluid.

Additionally, as the tip 62 is initially withdrawn from the aperture 58 in the stem 32, the fluid pressure behind the plug member 93 forces the plug member 93 against the tip 62. As the tip 62 is being withdrawn, the plug member 93 moves from the position of FIG. 6 to that of FIG. 5, and seats against the end 54 of the stem 32. At the time the seal between the plug member 93 and the stem 32 is re-established, the tip 62 of the instrument 22 and the aperture 58 in the stem 32 still form a hermetic seal. In other words, the tip 62 has not been completely withdrawn from the aperture 58. This sealing of the plug member 93 with the stem 32 before the tip 62 of the instrument 22 unseals with the stem 32 provides that the central axial fluid passageway 56 of the stem 32 becomes sealed off from area 105 providing, in effect, an intermediate volume. Thereafter, as the tip 62 is further withdrawn from the aperture 58, this intermediate volume increases resulting in a relatively low pressure area being formed in the central axial fluid passageway 56 before the tip 62 is disengaged from the stem 32 and the seal broken. Hence, the risk that fluid will spray out of the valve 10 through the aperture 58 when the seal between the tip 62 and the stem 32 is finally broken (upon the tip 62 being more fully withdrawn from the aperture 58) is reduced. This prevents the waste of fluid, reduces mess, and most importantly, prevents undue exposure of others to the fluid.

After the tip 62 has been fully removed from the aperture 58, the valve 10 looks again as shown in FIG. 4. At that time, the external surface of the end 48 of the stem 32, and the external surface of the end 20 of the valve body 12 can be wiped clean with a sterile swab, thus leaving no perceptible areas for bacteria growth. At this time, the valve 10 forms a positive seal urging the front body portion 34 of the stem 32 against the taper 90 at the end 20 of the valve body 12. As a result of this positive seal as well as the seal between the plug member 93 and the stem 32, if pressure is exerted on the fluid line (not shown) connected to the end 24 of the valve 10, the valve 10 will not leak. In fact, this pressure will further force the plug member 93 against the stem 32 and the stem 32 into the taper 90 thus enhancing or heightening the seals.

The above-described valve 10 provides several advantages over the prior art. For example, the neutral space 74 is sealed away from the fluid flow. Therefore, there is no leaking of fluid thereinto, and a compression spring, if provided between the stem 32 and the valve body 12, is not exposed to the flowing fluid. Also, the tip 62 of the instrument 22 is wiped virtually free of fluid upon the tip 62 being withdrawn from the valve 10. Additionally, the valve 10 provides no perceptible areas for bacterial growth. Still further, there is a reduced likelihood that fluid will spray from the valve 10 upon the withdrawal or insertion of an instrument 22. Many more advantages are provided by the present invention and have been previously described herein. Even more advantages may readily be realized by one having ordinary skill in the art.

While one embodiment of the invention has been described hereinabove, many modifications are entirely possible and anticipated. For example, the male rear portion 28 of the valve body 12 can be shaped for a male slip Luer connection with a fluid line. Alternatively, the male rear portion 28 of a valve body 12 may be provided with a male Luer lock thread thereon for engaging corresponding structure on a fluid line.

Additionally, many different apertures may be implemented in connection with the stem 32. For example, a first half of the aperture may have a ramp thereon for engaging a peaked flange on the other half of the aperture when the aperture closes. Alternatively, a first half of the aperture may have a squared slot thereon for engaging with a key on the other half of the aperture. Still further, a flap may be provided in the stem 32 for covering the aperture when the aperture closes. Still yet further, a first half of the aperture may have a curved slot thereon for engaging with a key on the other half of the aperture, or the first half of the aperture may have a peaked valley thereon for engaging a peaked flange on the other half of the aperture. These alternative apertures are depicted in U.S. application Ser. No. 09/151, 378, which has been already incorporated herein by reference. Of course, still other apertures may be used in accordance with the present invention.

While embodiments of the present invention are shown and described, it is envisioned that those skilled in the art may devise various modifications of the present invention without departing from the spirit and scope of the appended claims.

What is claimed is:

1. A valve engageable with an instrument, said valve comprising: a valve body; a deformable stem located in said valve body and shiftable therein, said stem having an aperture configured such that when the instrument is engaged with said aperture in said stem, said stem shifts within said valve body and said aperture deforms to allow liquid to flow therethrough to or from the instrument; a plug member in said stem, said plug member shiftable to a position of generally sealed engagement with said stem while the instrument is still engaged with said aperture in said stem.

2. A valve as recited in claim 1, wherein said plug member seals off a relatively high pressure area and provides a low pressure area adjacent said aperture thereby reducing a likelihood that fluid will squirt out said stem through said aperture when the instrument is disengaged from said aperture.

3. A valve as recited in claim 1, said stem and said valve body configured such that when the instrument is not engaged with said stem, said valve body engages said stem thereby urging said aperture closed.

4. A valve as recited in claim 1, wherein a portion of said stem is generally conical and facilitates the closing of said aperture in said stem when said valve body engages said stem when the instrument is not engaged with said stem.

5. A valve as recited in claim 1, said stem including a head portion, said head portion contacting said valve body when the instrument is not engaged in said aperture in said stem, said contact between said head portion and said valve body urging said aperture in said stem closed.

6. A valve as recited in claim 1, said stem including a throat portion which contacts said valve body and provides generally axial compressive resistance when the instrument is engaged with said aperture in said stem.

7. A valve as recited in claim 5, said stem including a throat portion which contacts said valve body and provides generally axial compressive resistance when the instrument is engaged with said aperture in said stem.

8. A valve as recited in claim 6, said throat portion including an end portion which sealably contacts said valve body.

9. A valve as recited in claim 7, said throat portion including an end portion which sealably contacts said valve body.

10. A valve as recited in claim 1, said valve body having stem-engaging structure on an internal surface thereof for engaging said stem when the instrument is not engaged with said aperture in said stem, said stem having valve-body engaging structure for engaging said stem-engaging structure on said valve body.

11. A valve as recited in claim 10, said stem-engaging structure on said valve body comprising a taper, said valve-body engaging structure on said stem comprising at least one contact point which engages said taper when the instrument is not engaged with said aperture in said stem.

12. A valve as recited in claim 11, said stem including a conical portion, a taper angle of said taper of said valve body being greater than a taper angle of said conical portion of said stem.

13. A valve as recited in claim 1, said stem having an end which has said aperture formed therein, said stem configured such that said end of said stem protrudes past an end of said valve body, thereby exposing said end of said stem when the instrument is not engaged with said aperture in said stem.

14. A valve engageable with an instrument having a tip portion, said valve comprising: a valve body; a deformable stem located in said valve body in a compressed condition and shiftable from a first position, said stem having an aperture configured such that when the instrument tip is engaged with said aperture in said stem, said stem is urged from the first position and said aperture deforms to allow liquid to flow therethrough to or from the instrument; a plug member disposed with a bore in the stem which generally seals with at least a portion of said stem when the valve is pressurized, but is capable of being displaced by said tip to unseat and permit fluid flow, yet will reseal as the instrument tip is being disengaged from said aperture in said stem.

15. A valve as recited in claim 14, wherein a portion of said stem is generally conical and facilitates the closing of said aperture in said stem when said stem is urged into said first position.

16. A valve as recited in claim 14, said stem including a head portion, said head portion contacting said valve body when said stem is urged into said first position, said contact between said head portion and said valve body urging said aperture in said stem closed.

17. A valve as recited in claim 16, said stem including a throat portion which contacts said valve body and provides generally axial compressive resistance when the instrument is engaged with said aperture in said stem and said stem is urged from said first position.

18. A valve as recited in claim 17, said throat portion including an end portion which sealably contacts said valve body.

19. A valve as recited in claim 14, wherein said plug member seals off a relatively high pressure area from said aperture in said stem and provides a low pressure area adjacent said aperture thereby reducing a likelihood that fluid will squirt out said stem through said aperture when the instrument is disengaged from said aperture in said stem.

20. A valve as recited in claim 14, said stem having an end which has said aperture formed therein, said stem configured such that said end of said stem protrudes past an end of said valve body, thereby exposing said end of said stem when said stem is in said first position.

* * * * *